US012127766B2

(12) United States Patent
Mickiewicz et al.

(10) Patent No.: US 12,127,766 B2
(45) Date of Patent: Oct. 29, 2024

(54) SELECTIVELY LOCKING POLYAXIAL SCREW

(71) Applicant: Medos International Sarl, Le Locle (CH)

(72) Inventors: Christopher Mickiewicz, Bridgewater, MA (US); Alec Manson, Boston, MA (US); Ellen Roberts, Mendon, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 17/685,364

(22) Filed: Mar. 2, 2022

(65) Prior Publication Data
US 2022/0280202 A1    Sep. 8, 2022

Related U.S. Application Data

(60) Provisional application No. 63/157,384, filed on Mar. 5, 2021.

(51) Int. Cl.
*A61B 17/70* (2006.01)
*A61B 17/86* (2006.01)

(52) U.S. Cl.
CPC ........ *A61B 17/7037* (2013.01); *A61B 17/704* (2013.01); *A61B 17/708* (2013.01); *A61B 17/7091* (2013.01); *A61B 17/8605* (2013.01)

(58) Field of Classification Search
None
See application file for complete search history.

(56) References Cited

U.S. PATENT DOCUMENTS

| 2,509,081 A | 5/1950 | Bluth et al. |
| 2,788,045 A | 4/1957 | Rosan |

(Continued)

FOREIGN PATENT DOCUMENTS

| DE | 29903342 U1 | 6/1999 |
| EP | 0470660 B1 | 7/1995 |

(Continued)

OTHER PUBLICATIONS

International Search Report and Written Opinion for Application No. PCT/EP2022/055328, dated Aug. 25, 2022 (15 pages).

(Continued)

*Primary Examiner* — Tessa M Matthews
(74) *Attorney, Agent, or Firm* — Barnes & Thornburg LLP

(57) ABSTRACT

The present disclosure generally relates to pedicle screws that can selectively lock polyaxial motion of a receiver head with a locking cap. The locking cap can allow locking of the polyaxial motion of the receiver member relative to the spherical head of the bone shank without having a rod placed in the rod slot of the receiver member. This can enable placement of the head of the pedicle screw in a desired position and orientation, locking the head in the desired position and orientation, and performing a maneuver, such as derotation, without a rod in place or any extra motion between the receiver member and the bone shank. In some embodiments, actuation of the locking cap can be achieved by rotating the locking cap relative to the receiver member, where rotation of the locking cap causes corresponding axial translation of the locking cap relative to the receiver member.

23 Claims, 12 Drawing Sheets

(56) References Cited

U.S. PATENT DOCUMENTS

| | | |
|---|---|---|
| 2,842,180 A | 7/1958 | Brown et al. |
| 4,124,318 A | 11/1978 | Sagady |
| 4,762,024 A | 8/1988 | Graft |
| 5,009,017 A | 4/1991 | Diekevers et al. |
| 5,102,412 A | 4/1992 | Rogozinski |
| 5,129,388 A | 7/1992 | Vignaud et al. |
| 5,154,719 A | 10/1992 | Cotrel |
| 5,281,223 A | 1/1994 | Ray |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried et al. |
| 5,643,260 A | 7/1997 | Doherty |
| 5,672,176 A | 9/1997 | Biedermann et al. |
| 5,683,390 A | 11/1997 | Metz-Stavenhagen et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 * | 8/2001 | Barker ............... A61B 17/7037 606/256 |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,829 B1 | 6/2004 | Bono et al. |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,896,677 B1 | 5/2005 | Lin |
| 6,905,500 B2 | 6/2005 | Jeon et al. |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,090,679 B2 | 8/2006 | Saint-Martin et al. |
| 7,125,426 B2 | 10/2006 | Moumene et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B1 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,316,684 B1 | 1/2008 | Baccelli et al. |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,479,156 B2 | 1/2009 | Lourdel et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,939 B2 | 5/2010 | Ludwig et al. |
| 7,717,942 B2 | 5/2010 | Schumacher |
| 7,722,649 B2 | 5/2010 | Biedermann et al. |
| 7,727,261 B2 | 6/2010 | Barker et al. |
| 7,731,736 B2 | 6/2010 | Guenther et al. |
| 7,736,380 B2 | 6/2010 | Johnston et al. |
| 7,766,945 B2 | 8/2010 | Nilsson et al. |
| 7,766,946 B2 | 8/2010 | Bailly |
| 7,776,072 B2 | 8/2010 | Barry |
| 7,780,703 B2 | 8/2010 | Yuan et al. |
| 7,785,354 B2 | 8/2010 | Biedermann et al. |
| 7,789,900 B2 | 9/2010 | Levy et al. |
| 7,806,914 B2 | 10/2010 | Boyd et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,172 B2 | 5/2011 | Chao et al. |
| 7,951,173 B2 | 5/2011 | Hammill, Sr. et al. |
| 7,951,175 B2 | 5/2011 | Chao et al. |
| 7,955,359 B2 | 6/2011 | Matthis et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,038,701 B2 | 10/2011 | Rock et al. |
| 8,052,724 B2 | 11/2011 | Jackson |
| 8,057,518 B2 | 11/2011 | Frasier et al. |
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,916 B2 | 1/2012 | Kumar et al. |

(56) References Cited

U.S. PATENT DOCUMENTS

| | | |
|---|---|---|
| 8,100,946 B2 | 1/2012 | Strausbaugh et al. |
| 8,114,134 B2 | 2/2012 | Winslow et al. |
| 8,157,846 B2 | 4/2012 | Randol et al. |
| 8,162,989 B2 | 4/2012 | Khalili |
| 8,162,991 B2 | 4/2012 | Strauss et al. |
| 8,167,910 B2 | 5/2012 | Nilsson |
| 8,167,912 B2 | 5/2012 | Jacofsky et al. |
| 8,167,914 B1 | 5/2012 | Hunt et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,303,602 B2 | 11/2012 | Biedermann et al. |
| 8,308,782 B2 | 11/2012 | Jackson |
| 8,313,515 B2 | 11/2012 | Brennan et al. |
| 8,313,516 B2 | 11/2012 | Konieczynski et al. |
| 8,337,530 B2 | 12/2012 | Hestad et al. |
| 8,343,191 B2 | 1/2013 | Matthis et al. |
| 8,377,100 B2 | 2/2013 | Jackson |
| 8,377,101 B2 | 2/2013 | Barrus et al. |
| 8,409,260 B2 | 4/2013 | Biedermann et al. |
| 8,430,914 B2 | 4/2013 | Spratt et al. |
| 8,460,308 B2 | 6/2013 | Marino et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,603,145 B2 | 12/2013 | Forton et al. |
| 8,608,746 B2 | 12/2013 | Kolb et al. |
| 8,632,571 B2 | 1/2014 | Kraus |
| 8,663,290 B2 | 3/2014 | Doubler et al. |
| 8,696,717 B2 | 4/2014 | Rock et al. |
| 8,828,060 B2 | 9/2014 | Biedermann et al. |
| 8,852,239 B2 | 10/2014 | Jackson et al. |
| 8,870,919 B2 | 10/2014 | Miller et al. |
| 8,876,869 B1 | 11/2014 | Schafer et al. |
| 8,900,240 B2 | 12/2014 | White et al. |
| 8,906,068 B1 | 12/2014 | Bedor |
| 8,945,189 B2 | 2/2015 | Barrus et al. |
| 8,951,294 B2 | 2/2015 | Gennari et al. |
| 8,986,349 B1 | 3/2015 | German et al. |
| 9,005,260 B2 | 4/2015 | Dauster et al. |
| 9,034,021 B2 | 5/2015 | Matthis et al. |
| 9,066,761 B2 | 6/2015 | McBride et al. |
| 9,078,715 B2 | 7/2015 | Biedermann et al. |
| 9,084,634 B1 | 7/2015 | Lab et al. |
| 9,155,567 B2 | 10/2015 | Auerbach et al. |
| 9,155,580 B2 | 10/2015 | Cormier et al. |
| 9,216,041 B2 | 12/2015 | Jackson et al. |
| 9,254,151 B2 | 2/2016 | Walker et al. |
| 9,259,247 B2 | 2/2016 | Chandanson et al. |
| 9,277,938 B2 | 3/2016 | Biedermann et al. |
| 9,314,280 B2 | 4/2016 | Corin |
| 9,393,048 B2 | 7/2016 | Carbone et al. |
| 9,402,673 B2 | 8/2016 | Cormier et al. |
| 9,433,445 B2 | 9/2016 | Ramsay et al. |
| 9,451,992 B2 | 9/2016 | Jensen et al. |
| 9,504,497 B2 | 11/2016 | Ark et al. |
| 9,510,862 B2 | 12/2016 | Montello et al. |
| 9,526,529 B2 | 12/2016 | Charvet |
| 9,554,829 B2 | 1/2017 | Cahill et al. |
| 9,642,654 B2 | 5/2017 | Reimels et al. |
| 9,649,134 B2 | 5/2017 | Hannen |
| 9,649,135 B2 | 5/2017 | Doubler et al. |
| 9,649,142 B2 | 5/2017 | Doubler et al. |
| 9,662,143 B2 | 5/2017 | Jackson |
| RE46,431 E | 6/2017 | Jackson |
| 9,700,354 B2 | 7/2017 | Jackson |
| 9,700,355 B2 | 7/2017 | Longtain et al. |
| 9,713,488 B2 | 7/2017 | Hutchinson |
| 9,724,130 B2 | 8/2017 | Chandanson et al. |
| 9,724,145 B2 | 8/2017 | Spratt et al. |
| 9,775,660 B2 | 10/2017 | Spratt et al. |
| 9,782,204 B2 | 10/2017 | Spratt et al. |
| 9,788,865 B2 | 10/2017 | Matthis et al. |
| 9,788,866 B2 | 10/2017 | Jackson |
| 9,801,665 B2 | 10/2017 | Jackson |
| 9,844,400 B2 | 12/2017 | Stevenson et al. |
| 9,918,747 B2 | 3/2018 | Spratt et al. |
| 9,943,338 B2 | 4/2018 | Biedermann et al. |
| 9,993,270 B2 | 6/2018 | Butler |
| 10,016,223 B2 | 7/2018 | Mishra |
| 10,039,572 B2 | 8/2018 | Harris et al. |
| 10,039,578 B2 | 8/2018 | Anderson et al. |
| 10,052,137 B2 | 8/2018 | Landry et al. |
| 10,058,354 B2 | 8/2018 | Jackson et al. |
| 10,064,657 B2 | 9/2018 | Spitler |
| 10,172,649 B2 | 1/2019 | Jackson et al. |
| 10,201,377 B2 | 2/2019 | Hutchinson |
| 10,226,282 B2 | 3/2019 | Spratt et al. |
| 10,251,677 B2 | 4/2019 | Heuer et al. |
| 10,258,390 B2 | 4/2019 | Biedermann et al. |
| 10,271,877 B2 | 4/2019 | Biedermann et al. |
| 10,299,836 B2 | 5/2019 | Daniels |
| 10,299,839 B2 | 5/2019 | Sicvol et al. |
| 10,321,938 B2 | 6/2019 | Chandanson et al. |
| 10,335,202 B2 | 7/2019 | Ziolo et al. |
| 10,342,582 B2 | 7/2019 | Spratt et al. |
| 10,357,289 B2 | 7/2019 | Biedermann et al. |
| 10,368,916 B2 | 8/2019 | May |
| 10,368,917 B2 | 8/2019 | Mishra et al. |
| 10,383,659 B2 | 8/2019 | Pham et al. |
| 10,413,342 B2 | 9/2019 | Spratt et al. |
| 10,426,520 B2 | 10/2019 | Biedermann et al. |
| 10,426,538 B2 | 10/2019 | Jones et al. |
| 10,441,328 B2 | 10/2019 | Petit |
| 10,456,173 B1 | 10/2019 | Casey et al. |
| 10,478,227 B2 | 11/2019 | Leff et al. |
| 10,478,228 B2 | 11/2019 | Kim et al. |
| 10,499,955 B2 | 12/2019 | Faulhaber |
| 10,499,957 B2 | 12/2019 | Jones et al. |
| 10,507,043 B1 | 12/2019 | Gladieux |
| 10,517,645 B2 | 12/2019 | van der Pol |
| 10,524,839 B2 | 1/2020 | Ahn |
| 10,555,759 B2 | 2/2020 | Krüger |
| 10,555,760 B2 | 2/2020 | Buttermann |
| 10,588,666 B2 | 3/2020 | Samuel et al. |
| 10,595,903 B2 | 3/2020 | Heuer |
| 10,603,081 B2 | 3/2020 | Harper et al. |
| 10,603,082 B2 | 3/2020 | Lish |
| 10,603,083 B1 | 3/2020 | Gladieux et al. |
| 10,610,260 B2 | 4/2020 | Biedermann et al. |
| 10,610,265 B1 | 4/2020 | Ark et al. |
| 10,631,901 B2 | 4/2020 | Fiechter et al. |
| 10,639,077 B2 | 5/2020 | Nichols et al. |
| 10,639,080 B2 | 5/2020 | Sharifi-Mehr et al. |
| 10,702,310 B2 | 7/2020 | Leff et al. |
| 10,716,609 B2 | 7/2020 | Biedermann et al. |
| 10,722,276 B2 | 7/2020 | Barrus et al. |
| 10,786,284 B2 | 9/2020 | Spratt et al. |
| 10,987,138 B2 | 4/2021 | Chandanson et al. |
| 10,987,145 B2 | 4/2021 | Hutchinson |
| 11,311,318 B2 | 4/2022 | Spratt et al. |
| 2002/0026193 A1 | 2/2002 | Barker et al. |
| 2002/0058942 A1 | 5/2002 | Biedermann et al. |
| 2002/0133159 A1 | 9/2002 | Jackson |
| 2003/0023243 A1 | 1/2003 | Biedermann et al. |
| 2003/0055426 A1 | 3/2003 | Carbone et al. |
| 2003/0073996 A1 | 4/2003 | Doubler et al. |
| 2003/0100896 A1 | 5/2003 | Biedermann et al. |
| 2003/0100904 A1 | 5/2003 | Biedermann |

(56) References Cited

U.S. PATENT DOCUMENTS

| | | |
|---|---|---|
| 2003/0125741 A1 | 7/2003 | Biedermann et al. |
| 2003/0153911 A1 | 8/2003 | Shluzas |
| 2003/0187433 A1 | 10/2003 | Lin |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2004/0249378 A1 | 12/2004 | Saint Martin et al. |
| 2004/0267264 A1 | 12/2004 | Konieczynski et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1 | 9/2005 | Biedermann et al. |
| 2005/0228326 A1 | 10/2005 | Kalfas et al. |
| 2005/0273101 A1 | 12/2005 | Schumacher |
| 2005/0277928 A1 | 12/2005 | Boschert |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0129149 A1 | 6/2006 | Iott et al. |
| 2006/0149241 A1 | 7/2006 | Richelsoph et al. |
| 2006/0161153 A1 | 7/2006 | Hawkes et al. |
| 2006/0195092 A1 | 8/2006 | Barry |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055240 A1 | 3/2007 | Matthis et al. |
| 2007/0055241 A1 | 3/2007 | Matthis et al. |
| 2007/0055244 A1 | 3/2007 | Jackson |
| 2007/0093826 A1 | 4/2007 | Hawkes et al. |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon et al. |
| 2007/0233078 A1 | 10/2007 | Justis et al. |
| 2007/0260246 A1 | 11/2007 | Biedermann |
| 2007/0265621 A1 | 11/2007 | Matthis et al. |
| 2007/0270806 A1 | 11/2007 | Foley et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1 | 7/2008 | Nilsson |
| 2008/0172062 A1 | 7/2008 | Donahue et al. |
| 2008/0200956 A1 | 8/2008 | Beckwith et al. |
| 2008/0215100 A1 | 9/2008 | Matthis et al. |
| 2008/0262556 A1 | 10/2008 | Jacofsky et al. |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1 | 11/2008 | Peterson et al. |
| 2008/0312692 A1 | 12/2008 | Brennan et al. |
| 2008/0319490 A1 | 12/2008 | Jackson |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0062861 A1 | 3/2009 | Frasier et al. |
| 2009/0062866 A1 | 3/2009 | Jackson |
| 2009/0088803 A1 | 4/2009 | Justis et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 | 8/2009 | Hutchinson |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264896 A1 | 10/2009 | Biedermann et al. |
| 2009/0264933 A1 | 10/2009 | Carls et al. |
| 2009/0287261 A1 | 11/2009 | Jackson |
| 2009/0318970 A1 | 12/2009 | Butler et al. |
| 2009/0326587 A1 | 12/2009 | Matthis et al. |
| 2010/0004693 A1 | 1/2010 | Miller et al. |
| 2010/0010540 A1 | 1/2010 | Park |
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0249846 A1 | 9/2010 | Simonson |
| 2010/0305621 A1 | 12/2010 | Wang et al. |
| 2010/0312279 A1 | 12/2010 | Gephart et al. |
| 2011/0046683 A1 | 2/2011 | Biedermann et al. |
| 2011/0098755 A1 | 4/2011 | Jackson et al. |
| 2011/0106179 A1 | 5/2011 | Prevost et al. |
| 2011/0152949 A1 | 6/2011 | Biedermann et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0257690 A1 | 10/2011 | Rezach |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1 | 2/2012 | Jackson et al. |
| 2012/0046701 A1 | 2/2012 | Gennari et al. |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1 | 5/2012 | Biedermann et al. |
| 2012/0143266 A1 | 6/2012 | Jackson et al. |
| 2012/0150239 A1 | 6/2012 | Garamszegi |
| 2012/0165881 A1 | 6/2012 | Biedermann et al. |
| 2012/0165882 A1 | 6/2012 | Biedermann et al. |
| 2012/0179209 A1 | 7/2012 | Biedermann et al. |
| 2012/0185003 A1 | 7/2012 | Biedermann et al. |
| 2012/0197313 A1 | 8/2012 | Cowan |
| 2012/0209336 A1 | 8/2012 | Jackson et al. |
| 2012/0215264 A1 | 8/2012 | Lee |
| 2012/0253404 A1 | 10/2012 | Timm et al. |
| 2012/0277805 A1 | 11/2012 | Farris |
| 2012/0303070 A1 | 11/2012 | Jackson |
| 2012/0310284 A1 | 12/2012 | Gerchow |
| 2012/0310290 A1 | 12/2012 | Jackson |
| 2012/0316605 A1 | 12/2012 | Palagi |
| 2012/0328394 A1 | 12/2012 | Biedermann et al. |
| 2012/0330364 A1 | 12/2012 | Jacofsky et al. |
| 2013/0013003 A1 | 1/2013 | Carbone et al. |
| 2013/0046350 A1 | 2/2013 | Jackson et al. |
| 2013/0053901 A1 | 2/2013 | Cormier et al. |

(56) References Cited

U.S. PATENT DOCUMENTS

| | | |
|---|---|---|
| 2013/0060294 A1 | 3/2013 | Donahue |
| 2013/0066380 A1 | 3/2013 | Haskins et al. |
| 2013/0072992 A1 | 3/2013 | Jackson et al. |
| 2013/0096618 A1 | 4/2013 | Chandanson et al. |
| 2013/0096623 A1 | 4/2013 | Biedermann et al. |
| 2013/0103093 A1 | 4/2013 | Biedermann et al. |
| 2013/0110172 A1 | 5/2013 | Biedermann et al. |
| 2013/0110180 A1 | 5/2013 | Doubler et al. |
| 2013/0123858 A1 | 5/2013 | Attia |
| 2013/0144346 A1 | 6/2013 | Jackson et al. |
| 2013/0144349 A1 | 6/2013 | Corin |
| 2013/0150904 A1 | 6/2013 | Biedermann et al. |
| 2013/0211467 A1 | 8/2013 | Dickinson |
| 2013/0238030 A1 | 9/2013 | Steib |
| 2014/0018861 A1 | 1/2014 | Hutchinson |
| 2014/0018867 A1 | 1/2014 | Freudiger et al. |
| 2014/0025119 A1 | 1/2014 | Biedermann et al. |
| 2014/0058458 A1 | 2/2014 | Barrus et al. |
| 2014/0094849 A1 | 4/2014 | Spratt et al. |
| 2014/0121703 A1 | 5/2014 | Jackson et al. |
| 2014/0142633 A1 | 5/2014 | Jackson et al. |
| 2014/0142634 A1 | 5/2014 | Schlaepfer et al. |
| 2014/0214097 A1 | 7/2014 | Jackson et al. |
| 2014/0228890 A1* | 8/2014 | Raju ............... A61B 17/8883 606/267 |
| 2014/0257409 A1 | 9/2014 | Reed |
| 2014/0277153 A1 | 9/2014 | Spratt et al. |
| 2014/0277157 A1 | 9/2014 | Chandanson et al. |
| 2014/0277158 A1 | 9/2014 | Spratt et al. |
| 2014/0277159 A1 | 9/2014 | Spratt et al. |
| 2014/0277161 A1 | 9/2014 | Spratt et al. |
| 2014/0277162 A1 | 9/2014 | Kostuik et al. |
| 2014/0277189 A1 | 9/2014 | Spratt et al. |
| 2015/0173816 A1 | 6/2015 | Biedermann et al. |
| 2016/0128733 A1 | 5/2016 | Spratt et al. |
| 2016/0135848 A1 | 5/2016 | Chandanson et al. |
| 2017/0049482 A1 | 2/2017 | Campbell et al. |
| 2017/0296235 A1 | 10/2017 | Chandanson et al. |
| 2017/0354446 A1 | 12/2017 | Spratt et al. |
| 2017/0354448 A1 | 12/2017 | Hutchinson |
| 2017/0360491 A1 | 12/2017 | Spratt et al. |
| 2018/0014863 A1 | 1/2018 | Biester et al. |
| 2018/0092666 A1 | 4/2018 | Wu et al. |
| 2018/0193063 A1* | 7/2018 | May ............... A61B 17/70 |
| 2018/0325569 A1 | 11/2018 | Ramsay et al. |
| 2019/0029731 A1 | 1/2019 | Shoshtaev |
| 2019/0038319 A1 | 2/2019 | Biedermann et al. |
| 2019/0150989 A1 | 5/2019 | Biester et al. |
| 2019/0150990 A1* | 5/2019 | Jackson ............. A61B 17/7035 |
| 2019/0209213 A1 | 7/2019 | Spratt et al. |
| 2019/0223917 A1 | 7/2019 | Gray et al. |
| 2019/0239936 A1 | 8/2019 | Hutchinson |
| 2019/0254717 A1 | 8/2019 | Chandanson et al. |
| 2019/0262044 A1 | 8/2019 | Roth et al. |
| 2019/0274738 A1 | 9/2019 | Heuer |
| 2019/0365426 A1 | 12/2019 | Spratt et al. |
| 2020/0038075 A1 | 2/2020 | Barrus et al. |
| 2020/0197052 A1 | 6/2020 | Heuer et al. |
| 2020/0367939 A1 | 11/2020 | Loftis et al. |
| 2021/0113246 A1 | 4/2021 | Biester et al. |
| 2021/0212730 A1 | 7/2021 | Chandanson et al. |
| 2021/0275232 A1 | 9/2021 | Keyer et al. |

FOREIGN PATENT DOCUMENTS

| | | |
|---|---|---|
| EP | 1295566 A1 | 3/2003 |
| EP | 0857465 B1 | 6/2003 |
| EP | 1570794 A1 | 9/2005 |
| EP | 1774919 B1 | 8/2008 |
| EP | 1795134 B1 | 8/2008 |
| EP | 1694229 B1 | 7/2010 |
| EP | 2208472 A1 | 7/2010 |
| EP | 2070485 B1 | 9/2011 |
| EP | 2272451 B1 | 4/2012 |
| EP | 2129310 B1 | 9/2012 |
| EP | 2286748 B1 | 5/2014 |
| EP | 2455028 B1 | 2/2016 |
| WO | 1991016020 A1 | 10/1991 |
| WO | 2004058081 A1 | 7/2004 |
| WO | 2004089245 A2 | 10/2004 |
| WO | 2005058173 A1 | 6/2005 |
| WO | 2008016892 A2 | 2/2008 |
| WO | 2008024937 A2 | 2/2008 |
| WO | 2008112114 A1 | 9/2008 |
| WO | 2008119006 A1 | 10/2008 |
| WO | 2009015100 A2 | 1/2009 |
| WO | 2009073655 A1 | 6/2009 |
| WO | 2010056846 A2 | 5/2010 |
| WO | 2011059732 A1 | 5/2011 |
| WO | 2011109009 A1 | 9/2011 |
| WO | 2011127065 A1 | 10/2011 |
| WO | 2012024665 A2 | 2/2012 |
| WO | 2012030712 A1 | 3/2012 |
| WO | 2012035479 A2 | 3/2012 |
| WO | 2012060868 A1 | 5/2012 |
| WO | 2013028851 A1 | 2/2013 |
| WO | 2016065033 A1 | 4/2016 |

OTHER PUBLICATIONS

International Search Report and Written Opinion for Application No. PCT/EP2022/053525, dated Jun. 23, 2022 (10 pages).

International Search Report and Written Opinion for Application No. PCT/EP/2022/055326, dated Jun. 14, 2022 (12 pages).

[No Author Listed] A New Angle on Correction. Expedium. DePuy. 2009. (2 pages).

[No Author Listed] Definition of "clip," www.thefreedictionary.com/clip; accessed May 16, 2015.

[No Author Listed] Expedium Spine System, Dual Innie Independent Locking Technology Brochure, DePuy Spine, Aug. 1, 2004, (6 pages).

[No Author Listed] Moss Miami Polyaxial Reduction Screw Surgical Technique, DePuy AcroMed, Inc., 1998.

[No Author Listed] Straight Talk with Expedium. Expedium, Jul. 2007 (10 pages).

[No Author Listed] Surgical Technique Guide and Ordering Information. Expedium. DePuy Spine Inc. Sep. 2011. (24 pages).

[No Author Listed] Value Analysis Brief—Expedium Favored Angle Screw. DePuy Synthes Spine. Aug. 2012. (4 pages).

[No Author Listed] Viper 2 MIS Extended Tab , DePuy Spine, Inc., Feb. 1, 2009.

[No Author Listed] Viper 2 MIS Spine System. System Guide. DePuy Spine Inc. Sep. 2011. 60 pages.

Duerig, T. W., et al., "An Engineer's Perspective of Pseudoelasticity," p. 370, in Engineering Aspects of Shape Memory Alloys, Butterworth-Heinemann, 1990.

International Search Report and Written Opinion for Application No. PCT/US2013/060350, dated Jan. 3, 2014 (9 pages).

International Search Report for PCT/US14/021198 dated Jun. 5, 2014 (3 pages).

International Preliminary Report on Patentability for Application No. PCT/US2014/021198, dated Sep. 24, 2015 (7 pages).

International Search Report and Written Opinion for Application No. PCT/EP2022/055326, dated Sep. 9, 2022 (14 pages).

U.S. Appl. No. 61/706,860, filed Sep. 28, 2012 (66 pages).

* cited by examiner

SELECTIVELY LOCKING POLYAXIAL SCREW

CROSS-REFERENCE TO RELATED APPLICATIONS

This application claims the benefit of U.S. Provisional Application No. 63/157,384, entitled "Selectively Locking Polyaxial Screw," filed on Mar. 5, 2021. The entire contents of this application are hereby incorporated by reference in their entirety.

FIELD

This disclosure relates generally to surgical instruments and methods of use, and, more particularly, to a bone anchor that uses a locking cap to selectively lock polyaxial movement of a receiver member head of the bone anchor relative to a shank without having a spinal rod placed in the receiver member.

BACKGROUND

During spine surgery, such as procedures to correct deformities in the spine, fixation constructs are often assembled to hold the spine in a desired shape. Such constructs often include a plurality of implanted bone anchors or pedicle screws along multiple vertebrae and a connecting spinal fixation element, such as a rod, that is received within a receiving member or head of each of the pedicle screws and secured using a set screw. In many cases, the pedicle screws are first implanted in the vertebrae, a rod is then positioned relative to the bone anchor heads, and set screws applied to secure the rod relative to each pedicle screw.

Current pedicle screw designs utilize various set screw locking methods. Single set screw designs allow a surgeon to lock polyaxial motion of the receiver head relative to the bone shank and constrain the rod within the receiver head in one step of locking the set screw. In dual set screw designs, a surgeon can lock polyaxial motion of the receiver head relative to the bone shank by tightening an outer portion of a dual set screw that contacts extended arms of a compression cap that reach around the rod to allow polyaxial movement locking without locking the rod against movement. The surgeon then has the flexibility to separately lock the rod relative to the receiver head by tightening an inner portion of the dual set screw that contacts the rod. Both the single set screw and dual set screw designs can require the rod to be placed in the receiver member of the pedicle screw prior to any polyaxial locking because the rod cannot be placed into the receiver head in a top-loading fashion after the set screw is threaded into the receiver head. That is, the standard pedicle screw transfers force from a set screw disposed proximal to a rod seat of the receiver member through one or more of a compression cap and a rod to the spherical head of the bone shank to lock against polyaxial motion of the bone shank relative to the receiver head of the pedicle screw.

There is a need for improved bone anchors that provide greater flexibility in selectively locking movement of a receiver member head relative to a shank.

SUMMARY

The present disclosure generally relates to a pedicle screw that can selectively lock polyaxial motion of a receiver head relative to a screw shank with a locking cap used in lieu of a conventional compression cap that transfers forces from a set screw and rod to achieve such a lock. The locking cap can allow a surgeon to selectively lock the polyaxial motion of the receiver member relative to the spherical head of the bone shank without having a rod placed in the rod slot of the receiver member and/or a set screw coupled to the receiver member. The instantly disclosed pedicle screw an prevent toggle of the receiver member during a manipulation prior to set screw tightening (e.g., during a derotation maneuver, etc.). When unlocked, the receiver member can move polyaxially relative to the bone shank and can toggle during manipulation of the spine due to the lack of a locked connection between the head and the shank. Use of the locking cap can enable the surgeon to place the head of the pedicle screw in a desired position and orientation, lock the head in the desired position and orientation, and perform a maneuver, such as derotation, without a rod in place or any extra motion between the receiver member and the bone shank.

In one aspect, a bone screw assembly is provided that includes a threaded shank having a proximal head portion, a receiver member disposed around the proximal head portion such that a distal portion of the threaded shank extends through a hole formed in a distal end of the receiver member, and a locking cap disposed in the receiver member proximal to the proximal head portion of the threaded shank. The locking cap can include one or more projections formed on an outer surface thereof that can be disposed within a thread form on an interior surface of the receiver member. The locking cap can move between an unlocked configuration, in which the receiver member can move polyaxially relative to the threaded shank, and a locked configuration, in which the receiver member is prevented from moving relative to the threaded shank. The interior surface of the receiver member can include a non-threaded portion proximal to the thread form that receives the one or more locking cap projections.

Any of a variety of alternative or additional features can be included and are considered within the scope of the present disclosure. For example, in some embodiments, the non-threaded portion can be disposed between the thread form and a second threaded portion formed along a proximal end portion of the interior surface of the receiver member. The thread form can include one or more keyways that intersect the thread form and extend axially along the interior surface of the receiver member to facilitate movement of the locking cap projections into the thread form. The keyways can intersect with a proximal-facing surface of a U-shaped recess formed in the receiver member.

In certain embodiments, the locking cap can contact the proximal head portion of the threaded shank when in the locked configuration. In some embodiments, the locking cap can rotate a half turn to move from the unlocked configuration to the locked configuration. In some embodiments, the locking cap can further include a drive feature on a proximal surface thereof. The locking cap can include two opposed projections in some embodiments. A distal-facing surface of the locking cap can have a profile complementary to a shape of the proximal head portion of the threaded shank. The proximal head portion of the threaded shank can have a spherical shape in some embodiments.

In some embodiments, the bone screw assembly can further include a spring clip seated within a groove formed in the interior surface of the receiver member and configured to impart a drag force to the proximal head portion of the threaded shank. In certain embodiments, the assembly can further include a spinal fixation rod disposed within a U-shaped recess formed in the receiver member proximal to the locking cap, and a set screw threadably coupled to the receiver member proximal to the spinal fixation rod. The spinal fixation rod can contact the locking cap and the set screw can contact the spinal fixation rod.

In another aspect, a surgical method is provided that includes disposing a threaded shank within a receiver member such that the threaded shank and receiver member can move polyaxially relative to one another, and distally advancing a locking cap into the receiver member through a proximal-facing opening past a non-threaded portion of an interior surface of the receiver member such that one or more projections formed on an exterior surface of the locking cap pass through one or more keyways formed in the interior surface of the locking cap and pass into a thread form in the interior surface of the receiver member. The method can further include rotating the locking cap to move between an unlocked configuration, in which the receiver member can move polyaxially relative to the threaded shank, and a locked configuration, in which the receiver member is prevented from moving relative to the threaded shank.

As with the instruments described above, the methods disclosed herein can include any of a variety of additional or alternative steps that are considered within the scope of the present disclosure. In some embodiments, for example, the method further includes implanting the threaded shank in a patient. In some embodiments, the threaded shank can be implanted in a vertebra.

In certain embodiments, the method can further include performing any of a derotation maneuver or a distraction maneuver after rotating the locking cap to move to the locked configuration. In some embodiments, the method can further include placing a spinal fixation rod within a U-shaped recess of the receiver member after rotating the locking cap to move to the locked configuration. Moreover, the method can further include threading a set screw into a threaded proximal end portion of the interior surface of the receiver member such that the set screw contacts the spinal fixation rod and the spinal fixation rod contacts the locking cap.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which.

DETAILED DESCRIPTION

Figure 1:
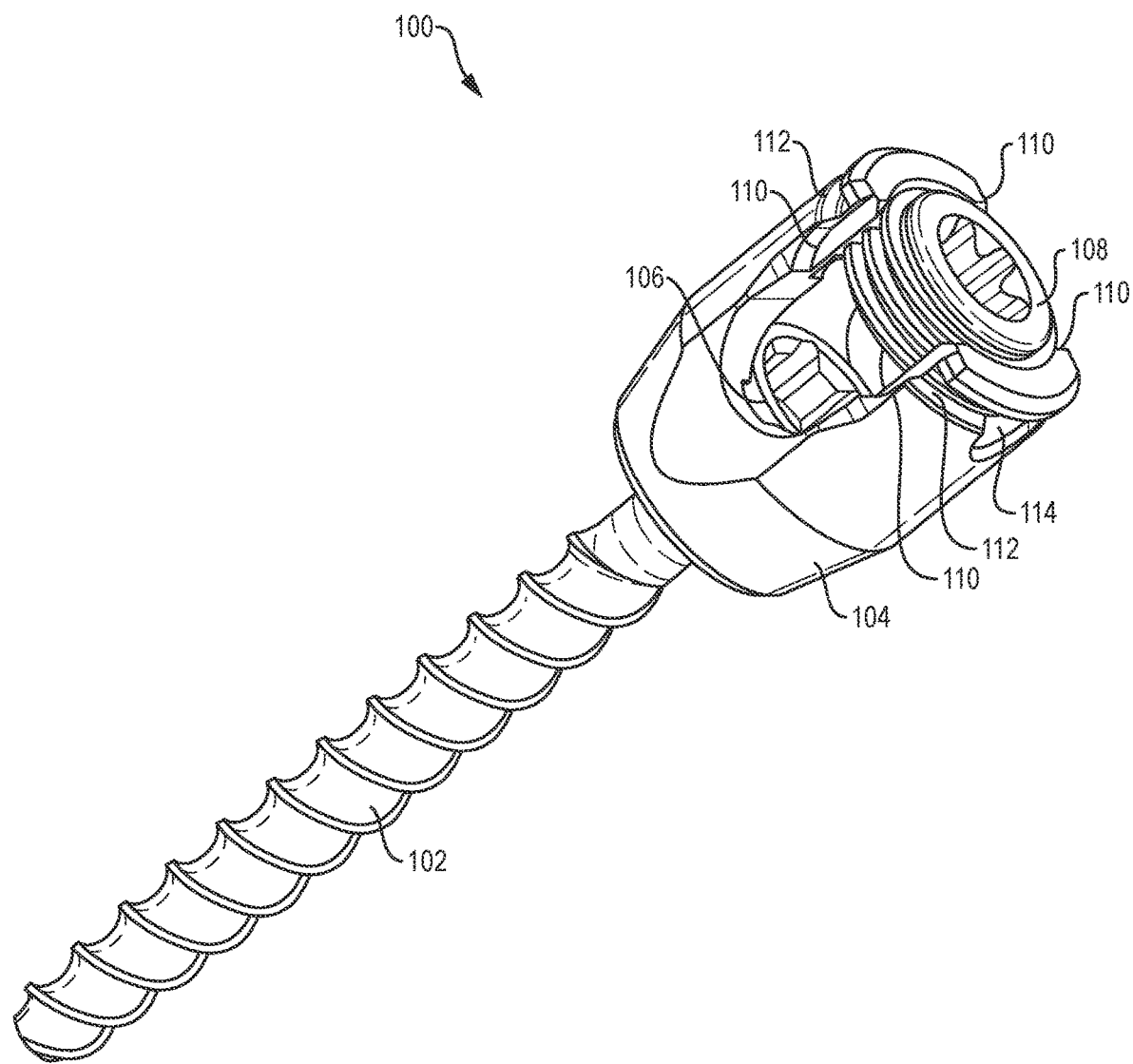
FIG. 1 is a perspective view of one embodiment of a selectively locking polyaxial screw of the present disclosure.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

The present disclosure generally relates to a pedicle screw design that can selectively lock polyaxial motion of a receiver head relative to a screw shank with a locking cap used in lieu of a conventional compression cap that transfers forces from a set screw and rod to achieve such a lock. The locking cap can allow a surgeon to selectively lock the polyaxial motion of the receiver member relative to the spherical head of the bone shank without having a rod placed in the rod slot of the receiver member. Moreover, the instantly disclosed pedicle screw prevents toggle of the receiver member during a manipulation prior to set screw tightening (e.g., during a derotation maneuver, etc.). When unlocked, the receiver member can move polyaxially relative to the bone shank and can toggle during a manipulation of the spine due to the lack of a locked connection between the head and the shank. Use of the locking cap enables placement of the head of the pedicle screw in a desired position and orientation, locking the head in the desired position and orientation, and performing a maneuver, such as derotation, without a rod in place or any extra motion between the receiver member and the bone shank.

For example, after implantation of a pedicle screw, the receiver member can be moved into a desired position and a driver can be used to tighten the locking cap to lock the polyaxial head to the shank and allow for manipulation of the vertebra in which the screw is implanted through the pedicle screw without the rod in place. This can be advantageous in certain cases, e.g., in cases where the spine is deformed such that a rod cannot be placed prior to deformity correction. Following rod placement, a standard set screw can be inserted into the receiver member and the implant can function like a standard pedicle screw where the spinal fixation rod transfers load from the set screw to the locking cap and bone shank to provide final locking of the pedicle screw.

Figure 2:
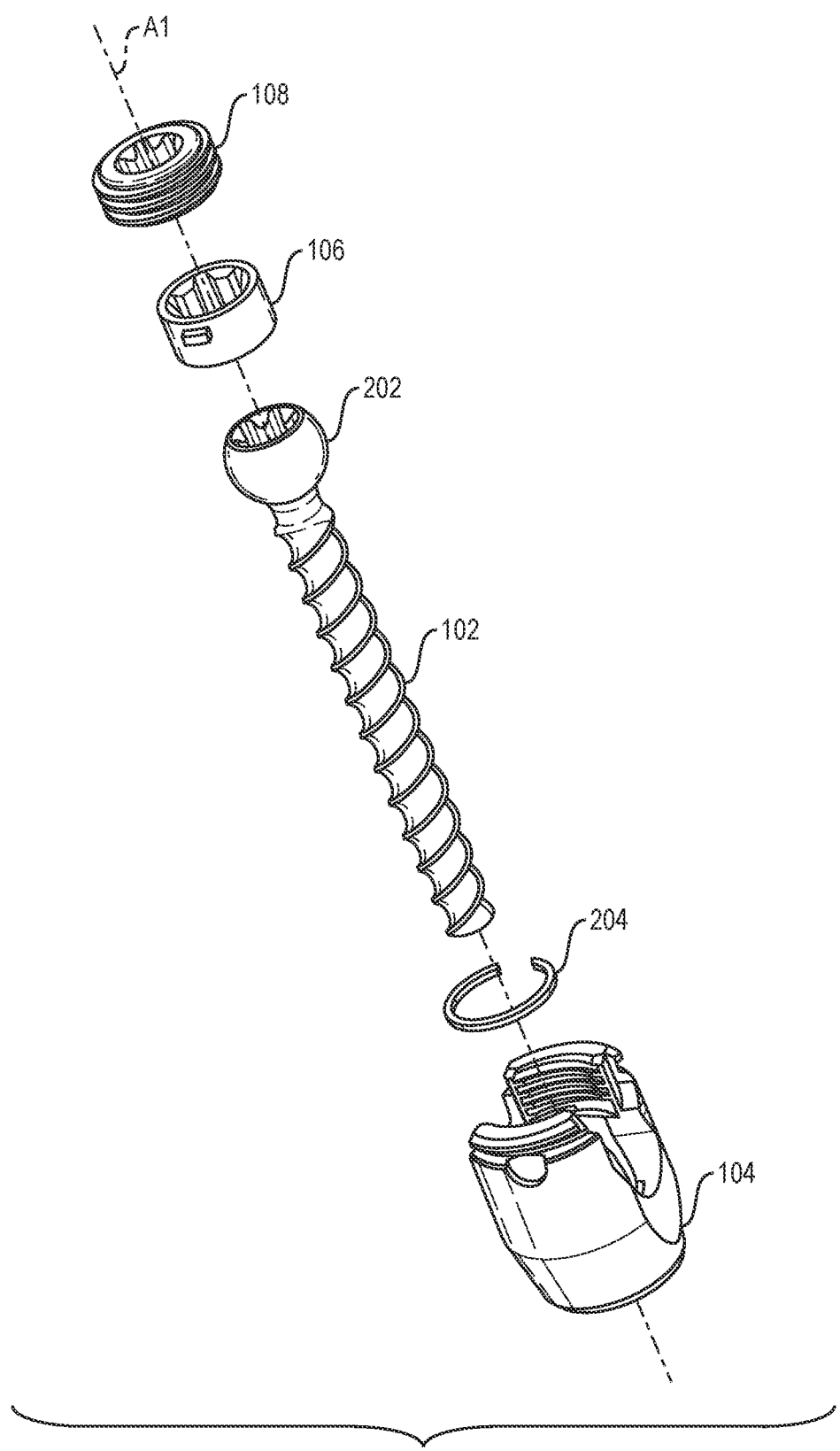
FIG. 2 is an exploded perspective view of the selectively locking polyaxial screw of FIG. 1.

FIGS. 1 and 2 illustrate one embodiment of a selectively locking polyaxial screw 100. As shown, the screw can include a bone shank 102 received in a distal opening of a receiver member 104 to couple thereto. The coupling between the shank and the receiver member 104 can occur by engaging a spherical head 202 of the bone shank with a locking cap or a locking screw 106. The locking cap 106 can engage a portion of the receiver member to lock the receiver member in a desired orientation relative to the shank 102 prior to insertion of a spinal rod. After locking, a spinal rod or another surgical device can be advanced distally to sit on a proximal end of the locking cap 106 and a set screw 108 can be advanced between the arms of the receiver member 104 to lock the spinal rod within the pedicle screw (see FIG. 11).

Figure 5:
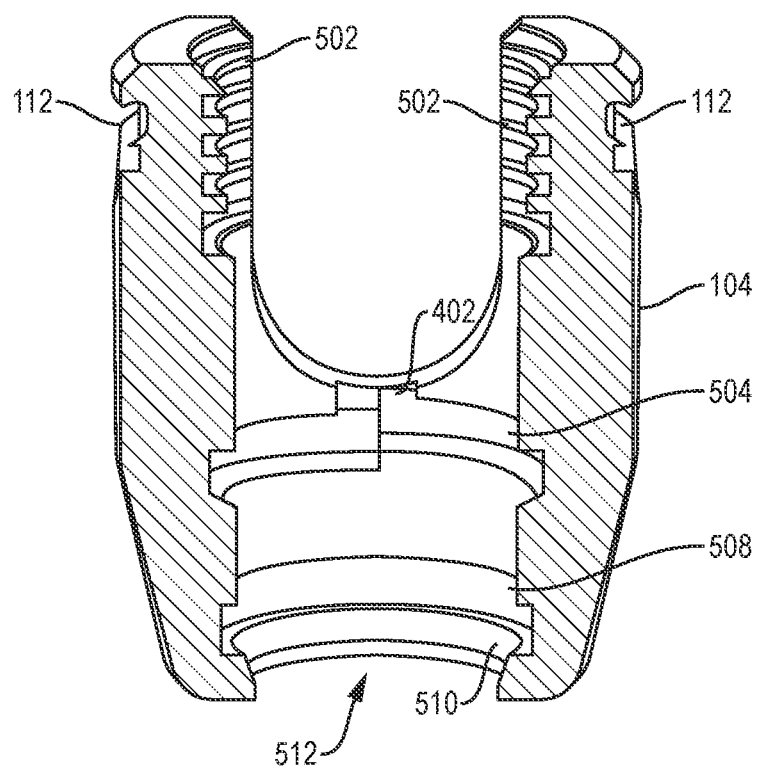
FIG. 5 is a side perspective cross-sectional view of the receiver member of FIG. 4 as taken along the line A-A.
Figure 6:
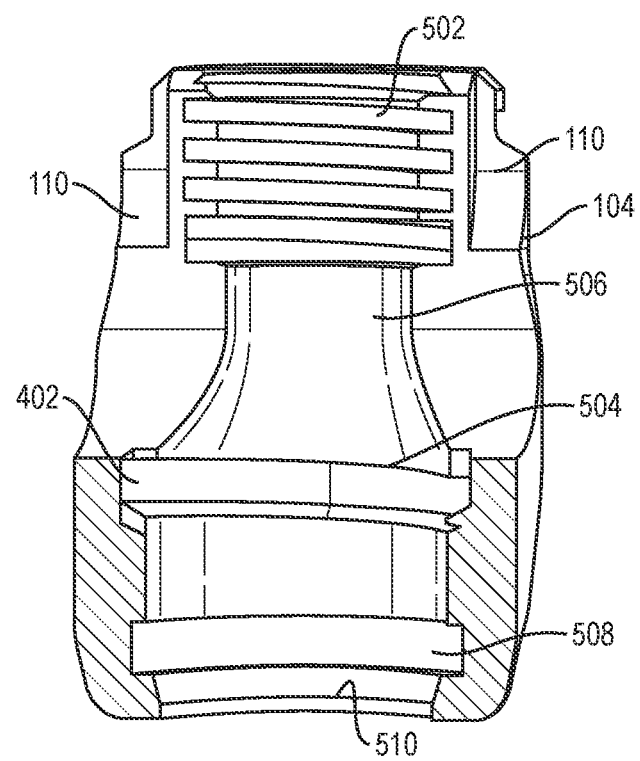
FIG. 6 is a side perspective cross-sectional detail view of the receiver member of FIG. 4 as taken along the line B-B.

As shown in FIG. 2, to assemble the screw 100 a spring clip 204 can be top loaded or advanced distally into an interior of the receiver member 104 until it sits within a groove formed therein (see FIGS. 5 and 6). The shank 102 can then be top loaded or advanced distally into the interior of the receiver member 104 until the distal bone-engaging portion of the shank 102 extends through a hole formed in the distal end of the receiver member 104, the proximal spherical head 202 is seated within a polyaxial seat formed in a distal end of the receiver member 104, and the spring clip 204 is frictionally engaged with the spherical head of the bone shank to provide a drag force resisting movement of the receiver member relative to the bone shank 102. The locking cap 106 can then be top loaded or advanced distally into the interior of the receiver member 104, as described in more detail below. Finally, a rod can be top loaded or advanced distally into the U-shaped recess formed between spaced apart arms of the receiver member 104 and the set screw 108 can be top loaded or advanced distally to engage with threads formed along a proximal interior portion of the receiver member to achieve final locking of the screw and rod.

FIGS. 1 and 2 also illustrate additional features of the receiver member 104, including the presence of unilateral holding features 110 at the lateral ends of each spaced apart arm of the receiver member 104. These features can interface with a unilateral holding instrument to allow gripping of the receiver member 104 in a manner that does not obstruct the proximal end opening of the U-shaped recess in the receiver member. This can be advantageous in connection with the selective locking features described herein, as any of a variety of manipulations can be performed without a rod placed in the receiver member 104 and while allowing the subsequent placement of such a rod using a top loading or distal advancement motion. Also shown is a groove or notch 112 formed around an outer surface of the spaced apart arms along a proximal portion of the receiver member 104, which can be utilized to couple any of a variety of instruments to the receiver head. Further, a rocker recess 114 is visible and shown intersecting the groove 112. A second rocker recess (not visible) can be formed on an opposite side of the receiver member and these recesses can be utilized to couple the receiver member to another surgical instrument, such as a rocker fork rod reducing instrument. Further details regarding other features of pedicle screws that can be included can be found in U.S. Pat. Nos. 10,039,578 and 10,299,839, as well as U.S. Provisional Appl. No. 63/157,362, entitled "Multi-Feature Polyaxial Screw" and filed on Mar. 5, 2021, and U.S. application Ser. No. 17/685,359, entitled "Multi-Feature Polyaxial Screw," filed on Mar. 2, 2022, and claiming priority to the previously-noted provisional application. The entire contents of each of these applications are incorporated by reference herein.

Figure 3A:
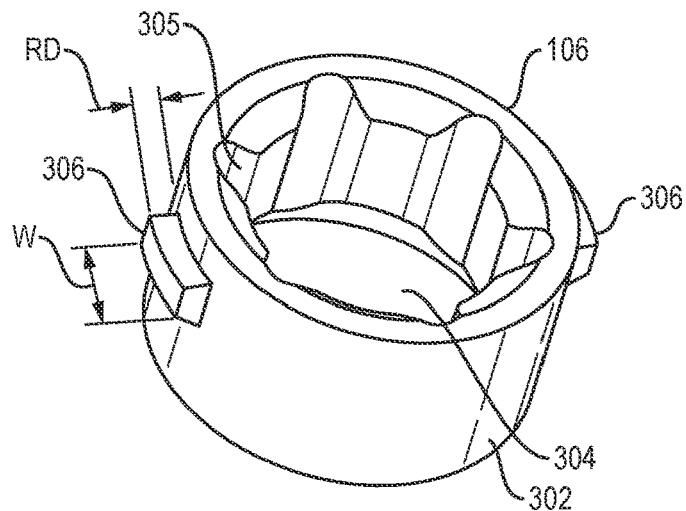
FIG. 3A is a top perspective view of the locking cap of the selectively locking polyaxial screw of FIG. 1.
Figure 3B:
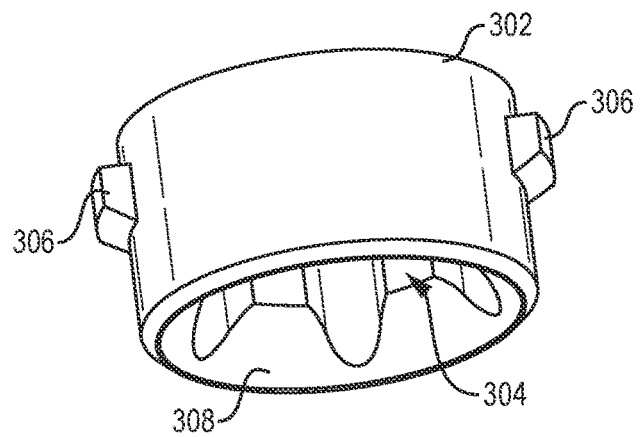
FIG. 3B is a side perspective view of the locking cap of FIG. 3A.
Figure 3C:
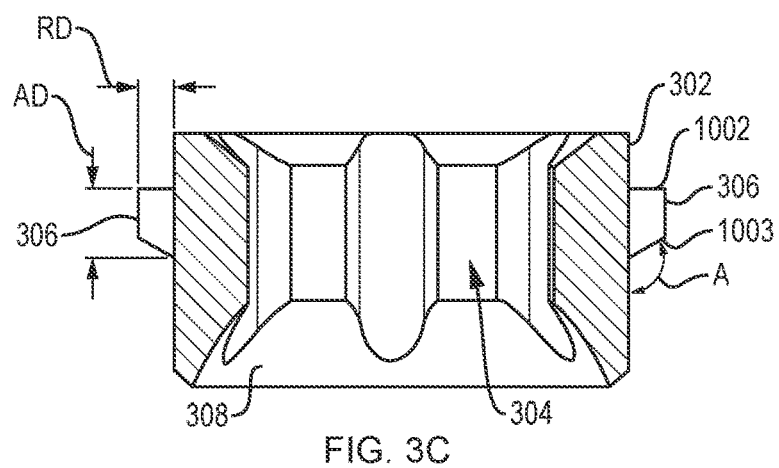
FIG. 3C is a side cross-sectional view of the locking cap of FIG. 3A.

FIGS. 3A-3C illustrate an example embodiment of the locking cap 106. As mentioned above, the locking cap 106 can be used in place of a conventional compression cap or saddle within the pedicle screw to selectively lock polyaxial movement of the shank 102 relative to the receiver member 104. As shown, the locking cap 106 can include a cylindrical body 302 having a channel 304 formed therein. At least a portion of the channel 304, e.g., the proximal end, can include a drive feature 305 for receiving one or more instruments therethrough that can rotate the locking cap. Example drive features can include hex drive features, square drive features, lobed drive features, etc. The driver used to rotate the locking cap 106 can be a screwdriver or similar component configured to rotate the locking cap 106 relative to the receiver member 104. As explained in more detail below, rotation of the locking cap 106 relative to the receiver member 104 can cause axial translation of the locking cap 106 due to interaction of a thread form in the receiver member 104 guiding a projection formed on the locking cap 106.

The locking cap 106 can include one or more projections or ears 306 extending from an outer surface of the cylindrical body 302. As shown, the projections 306 can extend in opposite directions from the outer surface of the body 302.

While two projections 306 are shown, an alternative number can be utilized (e.g., one, three, or more). In an embodiment where a larger number of projections 306 are utilized, they can be spaced evenly around the circumference of the body 302. Further, in some embodiments, the cylindrical body 302 of the locking cap 106 can include a continuous thread form extending around on an outer surface thereof in place of discrete projections.

The one or more projections 306 can have varying dimensions, including various widths W extending around the circumference of the cylindrical body 302, radial depths RD extending outward from the outer surface of the cylindrical body 302, and axial depths AD extending along a longitudinal axis of the cylindrical body 302. Further, the one or more projections can have varying shapes, including, for example, a proximal-facing surface 1002 that extends substantially perpendicularly from the outer surface of the cylindrical body 302, and a distal-facing surface 1003 that is angled obliquely relative to the outer surface of the cylindrical body 302. The angle A between the distal-facing surface 1003 and the outer surface of the cylindrical body 302 can vary and, in some embodiments, can be configured such that a radial measurement to the distal-facing surface 1003 increases in a proximal direction from a distal-most edge of the projection 306 (e.g., an angle A greater than 90° as shown) to facilitate introduction of the locking cap 106 into the receiver member 104.

The various dimensions of each projection 306 can vary in different embodiments, e.g., based on a circumference of the locking cap 106, the number of projections, etc. Generally speaking, it can be desirable to maximize a size of each projection 306 to maximize the strength thereof, but this must be balanced against a competing interest to minimize a size of any keyway or cutout formed in the receiver member 104 that receives each projection 306 during assembly. In some embodiments, a width W of a projection 306 can be selected to be less than a width of a rod-slot RSW (see FIG. 4) such that any keyway 402 formed in a receiver member 104 can have a keyway width KW that is less than the rod-slot width RSW. This can minimize material that is removed from the receiver member 104 when forming the keyway 402, thereby maximizing strength of the receiver member.

In some embodiments, the width W of each projection can extend through a radial arc of less than about 90°. In some embodiments, the width W of each projection can extend through a radial arc between about 45° and about 90° (resulting in between about ⅛ to about ¼ of a turn of the cap 106 to engage the projections with the receiver member 104). In some embodiments, the width W of each projection can extend through a radial arc of less than about 45°. Exact dimensions of the width W, radial depth RD, axial depth AD, and angle A of the distal-facing surface 1003 of each projection 306 can be varied based on a number of factors, such as overall screw size, number of projections, etc.

Figure 4:
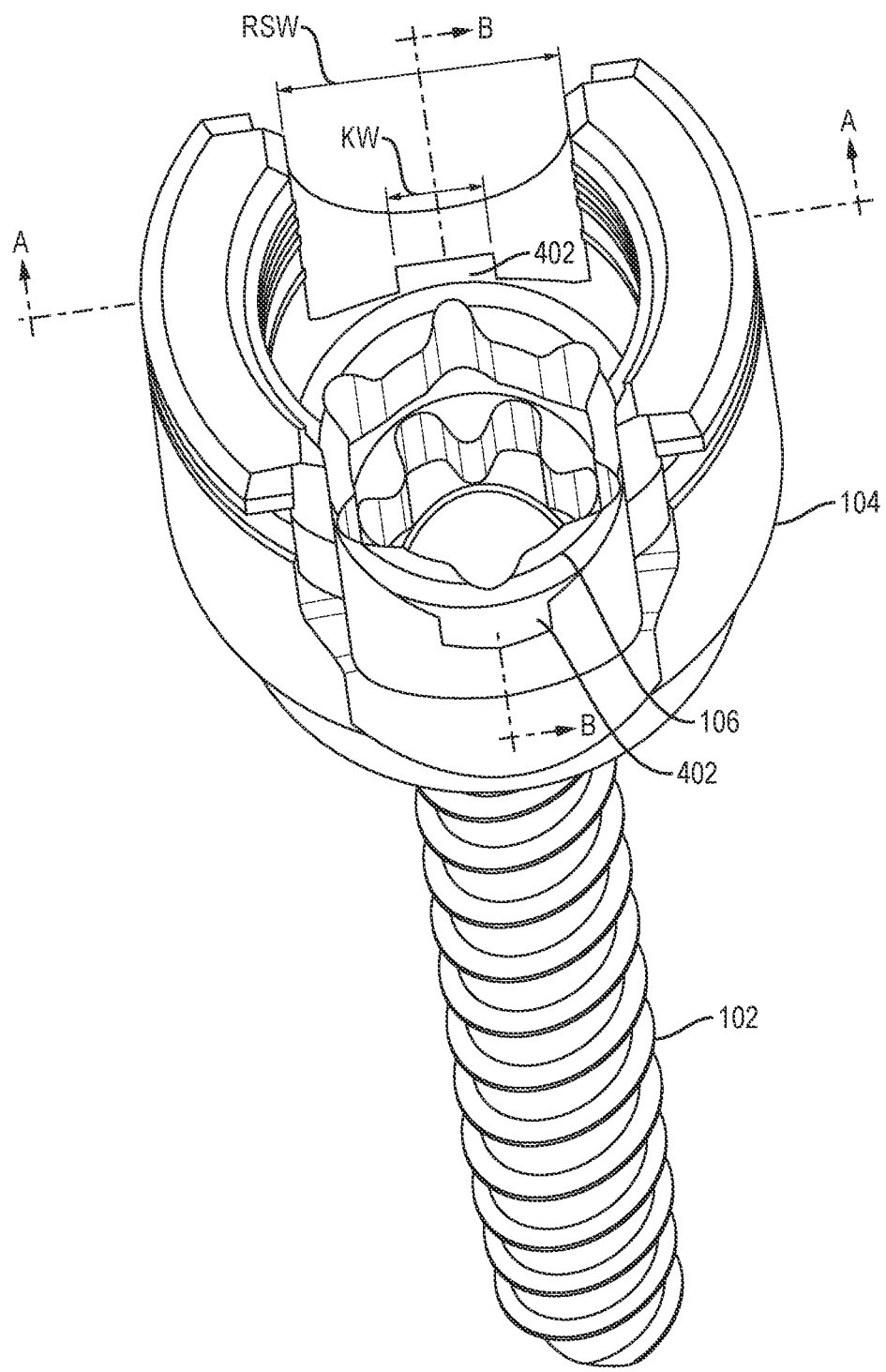
FIG. 4 is a top perspective view of the locking cap coupled to the receiver member of the selectively locking polyaxial screw of FIG. 1.

FIGS. 4-6 illustrate the receiver member 104 interior surfaces and interaction with the locking cap 106 in greater detail. As shown in FIGS. 5 and 6, which represent cross sectional views of the receiver member as taken along the lines A-A and B-B, respectively, shown in FIG. 4, the receiver member interior surface can include a proximal portion having a thread form 502 formed therein to receive a set screw 108. A further thread form 504 can be formed at a more distal location adjacent a distal end of the U-shaped recess defined by the spaced apart arms of the receiver member. Between the two thread forms, the receiver member 104 can include a smooth intermediate inner surface 506. Including the intermediate inner surface 506 can be advantageous because the absence of any thread form or other feature requiring removal of material can allow the receiver member wall to be at a maximum thickness, thereby maximizing stiffness of the receiver head. Also shown in FIGS. 5 and 6 are the groove 508 that receives the spring clip 204 and the polyaxial seat 510 that receives the spherical head 202 of the bone shank and defines the hole 512 formed in the distal end of the receiver member.

The thread form 504 that receives the protrusions 306 or other threading features of the locking cap 302 can allow the locking cap to ride along a surface thereof and control its position along a proximal-distal axis A1 (see FIG. 2), thereby controlling the frictional lock between the locking cap 106 and the head of the shank. The thread form 504 can include a variety of pitches based on the desired axial translation of the locking cap 106. The thread form 504 can also include a variety of rotations, including, in some embodiments, a single rotation or other configuration to allow quick locking or actuation of the locking cap 106 with one or less than one complete rotation of a driver. For example, in some embodiments the thread form 504 can be configured such that any of a quarter turn, half turn, or three-quarter turn of a driver is effective to actuate the locking cap 106 and selectively lock out polyaxial motion of a receiver head relative to a bone shank. In the illustrated embodiment, for example, a half turn of a driver is effective to actuate the locking cap 106.

The locking cap 106 can be inserted into the receiver member 104 by passing it distally from a proximal end of the receiver member such that the projections 306 are aligned with one or more keyways or slots 402 formed therein. The keyways 402 can allow the locking cap 106 to be translated distally from a proximal end of the receiver member 104 all the way to the thread form 504 without requiring any rotation of the locking cap 106. This can allow rapid assembly of the locking cap 106 to the receiver member 104 without requiring numerous turns of an actuating driver, which may not be possible if, for example, the entire interior surface of the receiver member included threads. The keyways or slots 402 can have a width KW sufficient to receive the width W of each projection 306 formed on the locking cap 106.

Once the locking cap 106 is advanced distally such that the projections 306 are received within the keyways 402 and aligned with the thread form 504, a driver can be used to rotate the locking cap 106 such that the projections 306 ride within the thread form 504 and control the further axial translation of the locking cap. The thread form 504 can be configured such that, as the projections 306 ride along the thread form 504 during rotation of the locking cap 106, the locking cap moves from an unlocked configuration, in which relative movement between the receiver member 104 and bone shank 102 are permitted, to a locked configuration, in which movement between the receiver member 104 and the bone shank 102 is prevented by frictional engagement between the locking cap distal surface 308 (see FIG. 3) and the spherical head 202 of the bone shank.

Figure 9:
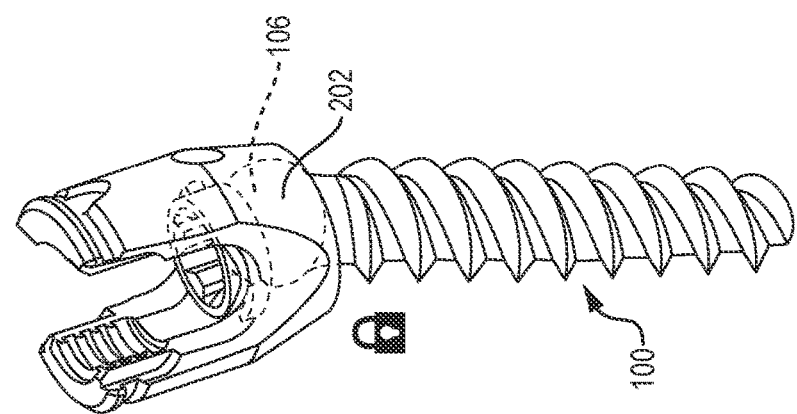
FIG. 9 is a perspective view of the selectively locking polyaxial screw of FIG. 1 in a locked configuration.
Figure 8:
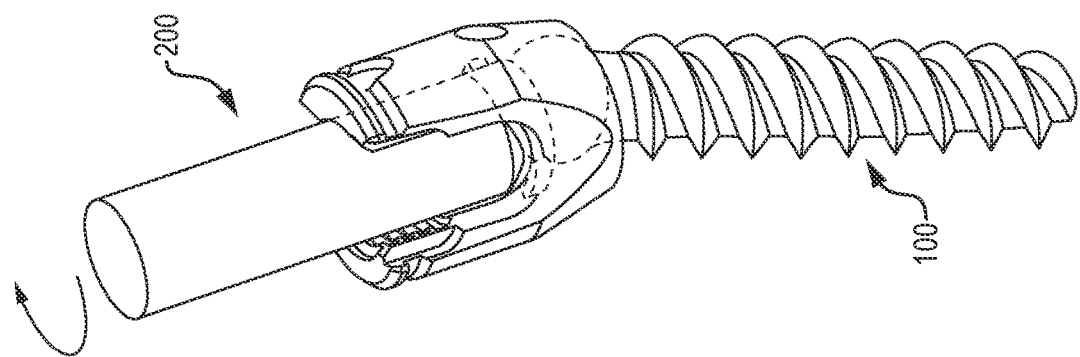
FIG. 8 is a perspective view of the selectively locking polyaxial screw of FIG. 1 with a driver coupled thereto.
Figure 7:
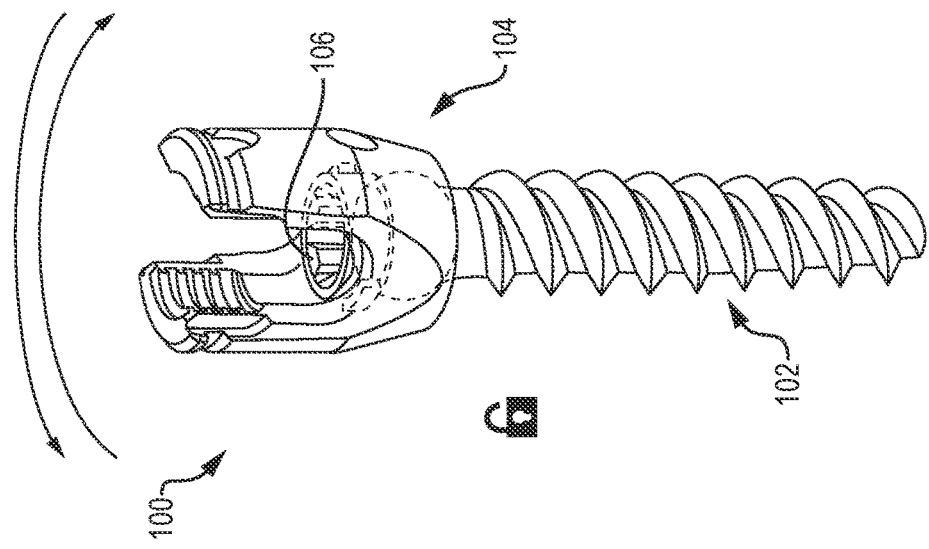
FIG. 7 is a perspective view of the selectively locking polyaxial screw of FIG. 1 in an unlocked configuration.

FIGS. 7-9 illustrate one embodiment of operation of the polyaxial screw 100. In FIG. 7, the screw is shown in an unlocked configuration where polyaxial movement of receiver member 104 relative to the bone shank 102 is permitted. This is because the locking cap 106 is positioned axially in a manner that it either does not contact the spherical head of the bone shank 102 or does so in a manner that does not exert sufficient frictional force to lock the position of the receiver member 104 relative to the bone shank 102. Note that it is possible to position the locking cap 106 in a manner that provides some degree of frictional engagement with the bone shank and therefore provides a provisional lock of the receiver member position that can be overcome by a user. In some embodiments, the drag clip 204 can provide such a provisional locking force in place of, or in addition to, the locking cap 106.

In FIG. 8, a driver instrument 200 is shown actuating the locking cap 106 by rotating it relative to the receiver member 104. As the driver instrument 200 rotates the locking cap 106, the projections 306 on the locking cap 106 with ride within the thread form 504 of the receiver member 104 and the locking cap 106 can move distally relative to the receiver member 104 in accordance with the axial pitch of the thread form 504. As the locking cap 106 advances distally during actuation, it can exert a greater frictional force on the spherical head of the bone shank 102 and effect a selective lock against polyaxial movement of the receiver member 104 relative to the bone shank 102. The driver instrument 200 can engage the locking cap 106 via the drive feature 305 on the proximal end of the locking cap 106. For example, the driver 200 can include a distal drive feature (not shown) that corresponds to the drive feature 305 on the proximal end of the locking cap 106 to allow rotation of the locking cap 106 relative to the polyaxial screw 100. The locking cap 106 can be rotated approximately a quarter turn, a half turn, a full turn, or more to actuate the locking cap 106.

Figure 10:
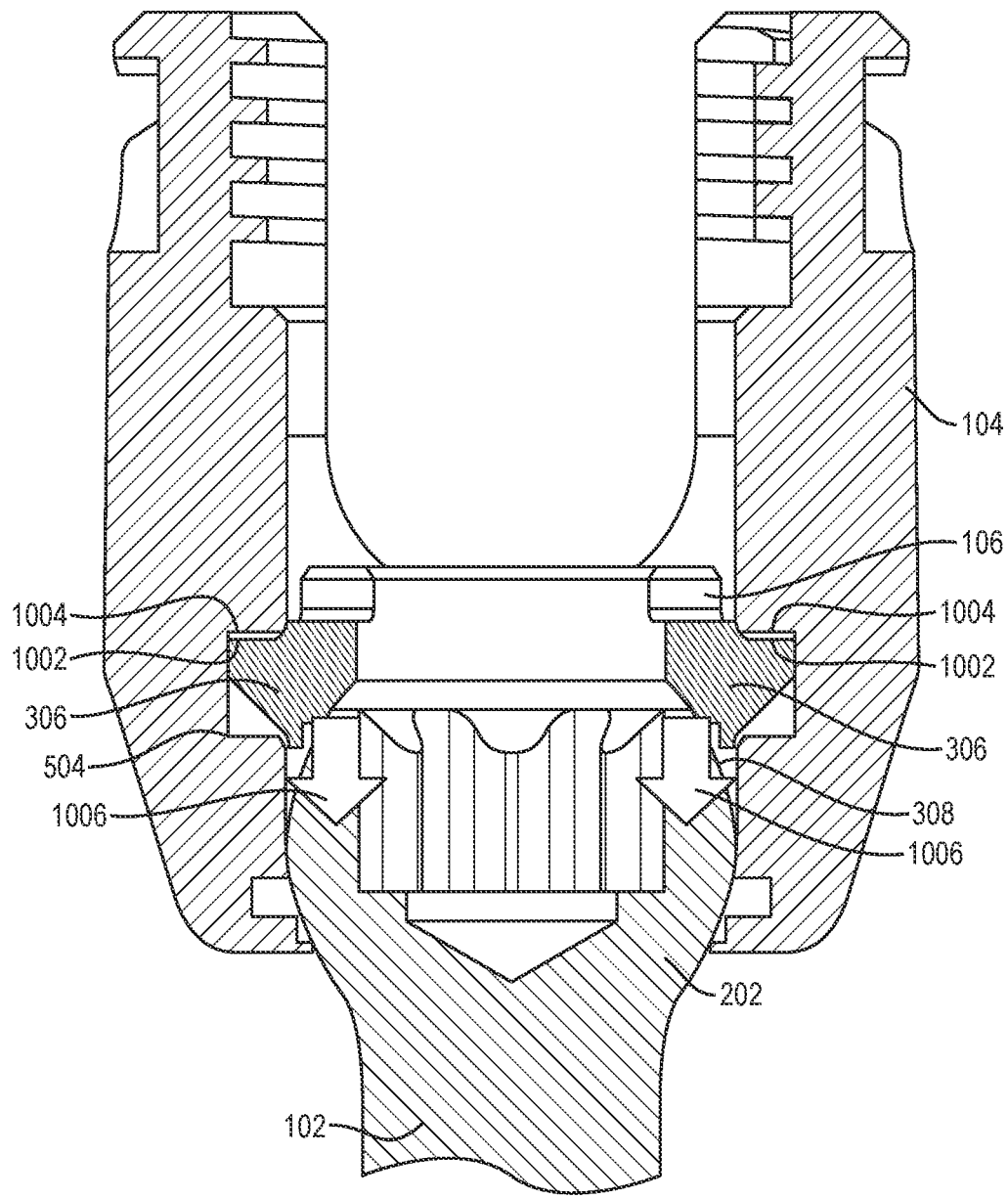
FIG. 10 is a side cross-sectional view of the receiver member, locking cap, and bone shank of the polyaxial screw of FIG. 1.

FIG. 9 illustrates the screw 100 in a locked configuration once the locking cap 106 has been fully actuated. In such a configuration, polyaxial movement of the receiver member 104 relative to the bone shank 102 is prevented by the frictional engagement of the locking cap 106 and spherical head 202 of the bone shank 102. FIG. 10 illustrates a cross-sectional view of the receiver member 104, locking cap 106, and bone shank 102 with spherical head 202. This view illustrates the proximal-facing surfaces 1002 of the projections 306 engaging distal-facing surfaces 1004 of the thread form 504 in order to urge the locking cap 106 distally (as shown by arrows 1006) and impart a frictional force onto the spherical head 202 of the bone shank. As mentioned above, unlike a conventional compression cap which transfers force from a set screw and rod to the shank to lock the polyaxial motion, the locking cap 106 can lock the receiver member 104 relative to the shank without a rod or set screw in place. This is because the projections of the locking cap 106 can form a shoulder that abuts a surface of the thread form 504 to prevent proximal translation of the locking cap 106 relative to the receiver member 104. A distal surface 308 of the locking cap can engage the spherical head 202 of the bone shank to force a coupling between the locking cap and the spherical head of the shank.

Figure 11:
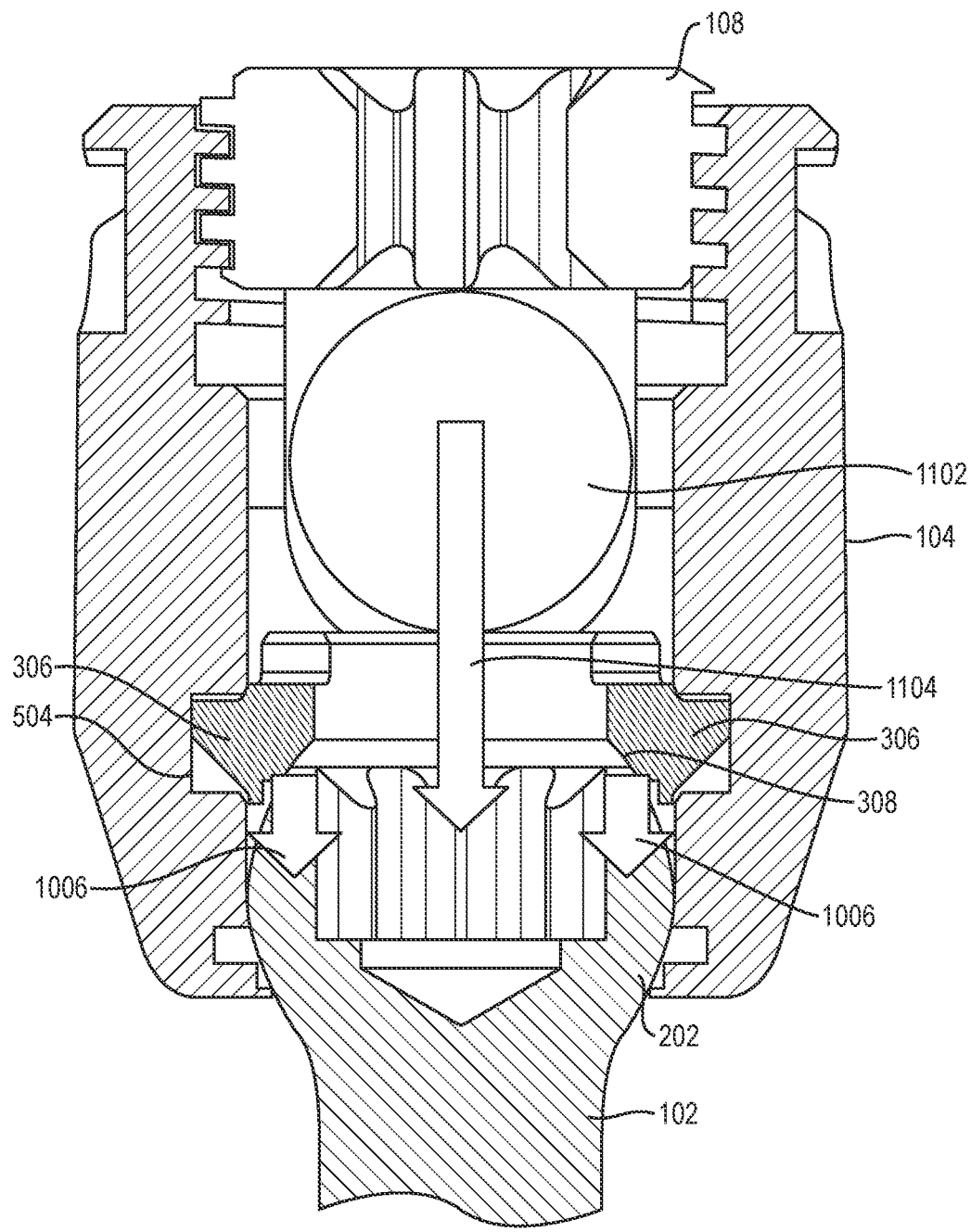
FIG. 11 is a side cross-sectional view of the assembly of FIG. 10 with a spinal rod and set screw disposed therein.

Note also that a height of the thread form 504 can be greater than a height of the projections 306 such that additional distal translation of the locking cap 106 is possible. Such additional distal translation can be achieved using a set screw and rod force transfer in the manner of a conventional polyaxial screw, as shown in FIG. 11. As a result, the locking cap 106 provides a further advantage in that it can function in the same manner as a conventional compression cap after a rod and set screw are placed in the receiver member U-shaped opening. That is, a final locking of the polyaxial screw, with potentially even greater locking force than can be achieved with the locking cap 106, can be achieved without requiring further direct manipulation of the locking cap 106. A spinal fixation rod 1102 and set screw 108 can be placed in the U-shaped recess of the receiver member 104 and the set screw tightened. As the set screw bears distally down on the rod, the rod can bear distally down on the locking cap 106, as shown by arrow 1104. Given the freedom for additional distal translation provided by the difference in height between the thread form 504 and the locking cap projections 306, the locking cap can be urged distally by the force from the rod and set screw, thereby engaging a distal end 308 of the locking cap 106 with the spherical head 202 of the bone shank 102. With such a configuration, the set screw and rod can assume the load for locking the screw and relieve any force exerted between the proximal-facing surfaces 1002 of the locking cap projections and the distal-facing surfaces 1004 of the thread form 504.

Figure 12:
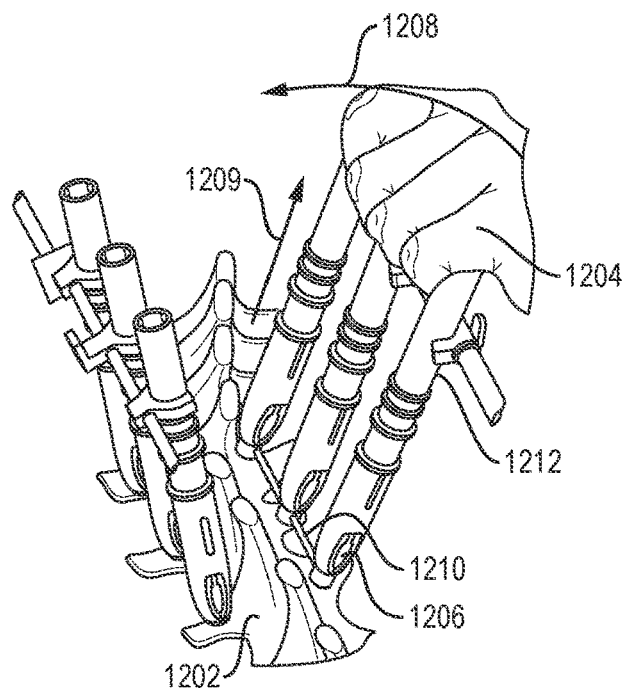
FIG. 12 is a perspective view of one embodiment of a derotation maneuver performed by selectively locking pedicle screws against polyaxial movement and manipulating vertebrae using the implanted pedicle screws.
Figure 13:
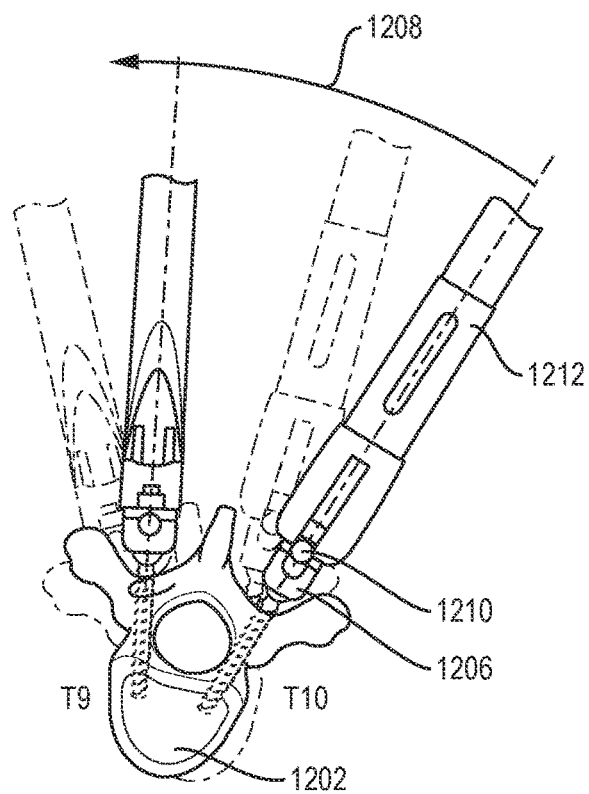
FIG. 13 is a transverse plane cross-sectional view of the maneuver of FIG. 12.

FIGS. 12-16 illustrate various procedures that can be performed using the polyaxial screws of the present disclosure. For example, FIGS. 12 and 13 show derotation maneuvers that can be performed by selectively locking pedicle screws against polyaxial movement and pulling or rotating vertebrae using the implanted pedicle screws. For example, FIG. 12 illustrates a perspective view of a surgeon or other user manipulating a group of vertebrae 1202 by exerting forces from their hand 1204 onto a group of implanted pedicle screws 1206 implanted in the vertebrae, e.g., to move the vertebrae in the direction of arrows 1208, 1209. When performing such maneuvers, it can be desirable to lock one or more implanted pedicle screws against polyaxial movement that can create toggling of a receiver member relative to an implanted screw shank when force is applied thereto. FIG. 13 illustrates a transverse plane view of the maneuver of FIG. 12. In the maneuvers shown in FIGS. 12 and 13, however, a spinal fixation rod 1210 is shown placed in the U-shaped recess of each pedicle screw and instrumentation 1212 is attached thereto that obstructs the proximal end opening of the U-shaped recess of each pedicle screw 1206. Accordingly, the selectively locking polyaxial screws disclosed herein can provide additional advantages in similar maneuvers, since they can be performed prior to rod and/or set screw placement and can utilize extension instrumentation that couples to the receiver members on only one side thereof (e.g., using unilateral attachment feature 110) to preserve access to the proximal end of the U-shaped opening. Examples of such extension instrumentation are provided in U.S. Pat. No. 10,966,762, the entire contents of which are incorporated by reference herein.

Figure 14:
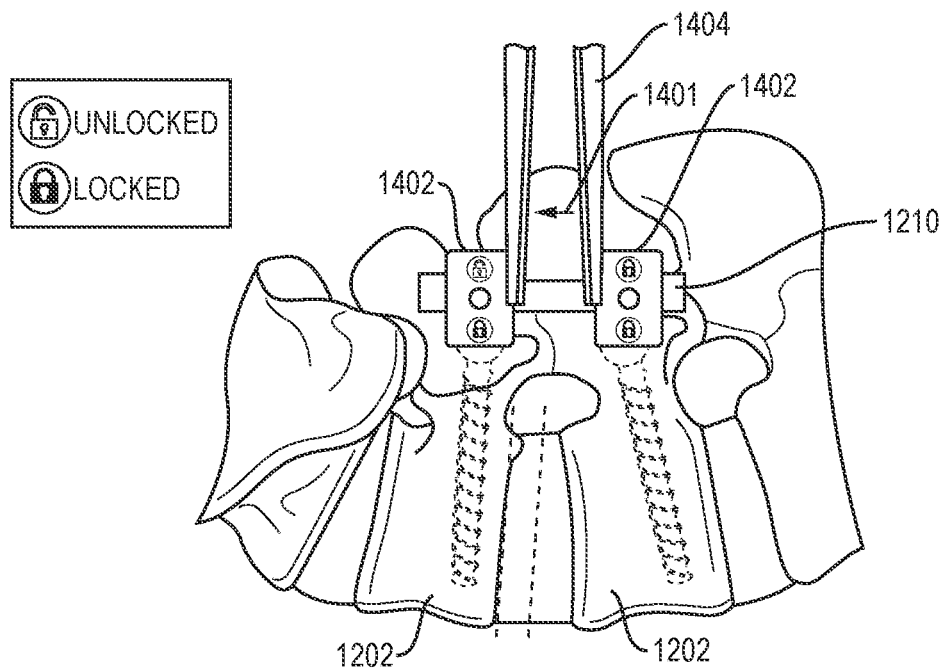
FIG. 14 is a sagittal plane view of one embodiment of a parallel compression/distraction maneuver using forceps and implanted pedicle screws to adjust relative positions of the vertebrae.
Figure 15:
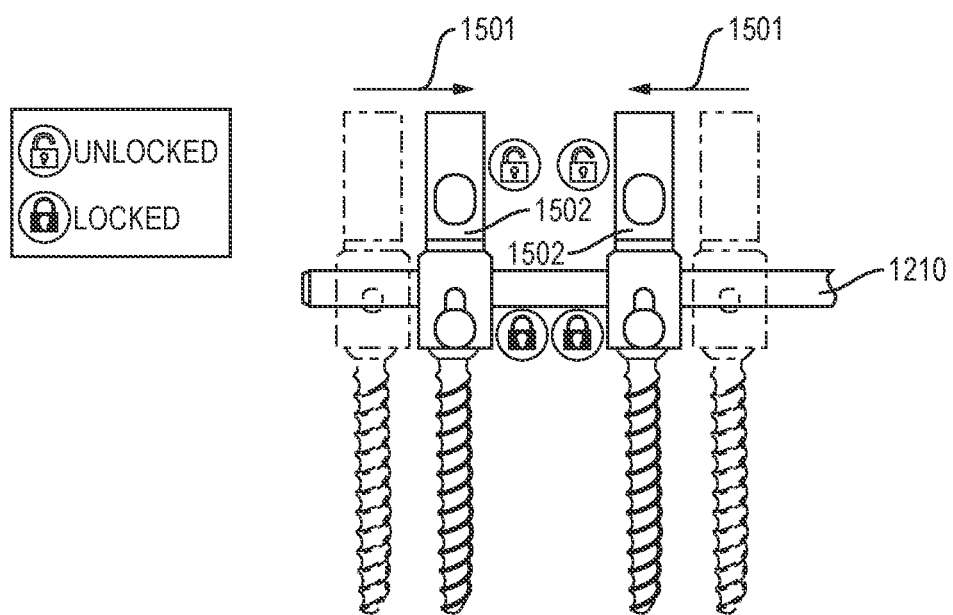
FIG. 15 is a sagittal plane view of another embodiment of a parallel compression/distraction movement.
Figure 16:
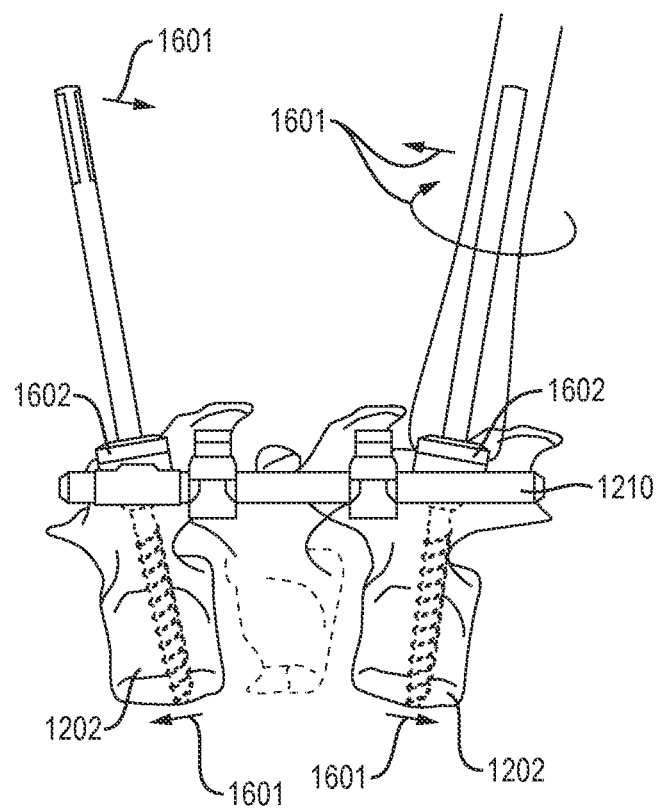
FIG. 16 is sagittal plane cross-sectional view of one embodiment of a trauma-correction maneuver.

FIGS. 14-16 illustrate various distraction, compression, and trauma-correction maneuvers that can also be facilitated using the selective locking screws disclosed herein. In such maneuvers, implanted pedicle screws 1402, 1502, 1602 can be locked against polyaxial movement and forceps 1404 or other extension instrumentation can be coupled to the screws and utilized to exert forces that adjust relative positions of vertebrae, e.g., increase or decrease a distance or angle therebetween, etc., as shown by arrows 1401, 1501, 1601. In such embodiments, one or more surgical instruments can be attached to the screws and rotated and/or translated relative to one another so as to align the vertebrae in a desired direction. Across a variety of maneuvers, selectively locking screws as disclosed herein can provide surgeons with flexibility to perform maneuvers before or after rod placement, which can be a significant advantage over conventional instrumentation and techniques.

The instruments disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/ replacement, and reassembly. Use of such techniques, and the resulting reconditioned device, are all within the scope of the present disclosure.

The devices described herein can be processed before use in a surgical procedure. For example, a new or used instrument or component can be obtained and, if necessary, cleaned. The instrument or component can be sterilized. In one sterilization technique, the instrument or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the instrument or component and in the container. The sterilized instrument or component can then be stored in the sterile container. The sealed container can keep the instrument or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different portions of the device or component due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are incorporated by reference in their entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A bone screw assembly, comprising:
    a threaded shank having a proximal head portion;
    a receiver member disposed around the proximal head portion such that a distal portion of the threaded shank extends through a hole formed in a distal end of the receiver member; and
    a locking cap disposed in the receiver member proximal to the proximal head portion of the threaded shank, the locking cap including one or more projections formed on an outer surface thereof that are disposed within a thread form on an interior surface of the receiver member;
    wherein the locking cap moves between an unlocked configuration, in which the receiver member can move polyaxially relative to the threaded shank, and a locked configuration, in which the receiver member is prevented from moving relative to the threaded shank;
    wherein the interior surface of the receiver member includes a non-threaded portion proximal to the thread form that receives the one or more locking cap projections.
2. The assembly of claim 1, wherein the non-threaded portion is disposed between the thread form and a second threaded portion formed along a proximal end portion of the interior surface of the receiver member.
3. The assembly of any of claims 1 to 2, wherein the thread form includes one or more keyways that intersect the thread form and extend axially along the interior surface of the receiver member to facilitate movement of the locking cap projections into the thread form.
4. The assembly of claim 3, wherein the keyways intersect with a proximal-facing surface of a U-shaped recess formed in the receiver member.
5. The assembly of any of claims 1 to 4, wherein the locking cap contacts the proximal head portion of the threaded shank when in the locked configuration.
6. The assembly of any of claims 1 to 5, wherein the locking cap rotates a half turn to move from the unlocked configuration to the locked configuration.
7. The assembly of any of claims 1 to 6, wherein the locking cap further comprises a drive feature on a proximal surface thereof.
8. The assembly of any of claims 1 to 7, further comprising a spring clip seated within a groove formed in the interior surface of the receiver member and configured to impart a drag force to the proximal head portion of the threaded shank.
9. The assembly of any of claims 1 to 8, further comprising:
    a spinal fixation rod disposed within a U-shaped recess formed in the receiver member proximal to the locking cap; and
    a set screw threadably coupled to the receiver member proximal to the spinal fixation rod.
10. The assembly of claim 9, wherein the spinal fixation rod contacts the locking cap and the set screw contacts the spinal fixation rod.
11. The assembly of any of claims 1 to 10, wherein the locking cap includes two opposed projections.
12. The assembly of any of claims 1 to 11, wherein a distal-facing surface of the locking cap has a profile complementary to a shape of the proximal head portion of the threaded shank.
13. The assembly of claim 12, wherein the proximal head portion of the threaded shank has a spherical shape.

14. A surgical method, comprising:
   disposing a threaded shank within a receiver member such that the threaded shank and receiver member can move polyaxially relative to one another;
   distally advancing a locking cap into the receiver member through a proximal-facing opening past a non-threaded portion of an interior surface of the receiver member such that one or more projections formed on an exterior surface of the locking cap pass through one or more keyways formed in the interior surface of the locking cap and pass into a thread form in the interior surface of the receiver member; and
   rotating the locking cap to move between an unlocked configuration, in which the receiver member can move polyaxially relative to the threaded shank, and a locked configuration, in which the receiver member is prevented from moving relative to the threaded shank.

15. The method of claim 14, further comprising implanting the threaded shank in a patient.

16. The method of claim 15, wherein the threaded shank is implanted in a vertebra.

17. The method of claim 16, further comprising performing any of a derotation maneuver or a distraction maneuver after rotating the locking cap to move to the locked configuration.

18. The method of any of claims 14 to 17, further comprising placing a spinal fixation rod within a U-shaped recess of the receiver member after rotating the locking cap to move to the locked configuration.

19. The method of claim 18, further comprising threading a set screw into a threaded proximal end portion of the interior surface of the receiver member such that the set screw contacts the spinal fixation rod and the spinal fixation rod contacts the locking cap.

What is claimed is:

1. A bone screw assembly, comprising:
   a threaded shank having a proximal head portion;
   a receiver member disposed around the proximal head portion such that a distal portion of the threaded shank extends through a hole formed in a distal end of the receiver member; and
   a unitary locking cap disposed in the receiver member proximal to the proximal head portion of the threaded shank, the locking cap including one or more projections formed on an intermediate portion of the outer surface thereof that are disposed within a thread form on an interior surface of the receiver member, the outer surface of the locking cap extending proximal and distal to the intermediate portion, and the one or more projections having a width that extends through a radial arc of less than about 90';
   wherein the locking cap moves between an unlocked configuration, in which the receiver member can move polyaxially relative to the threaded shank, and a locked configuration, in which the receiver member is prevented from moving relative to the threaded shank;
   wherein the interior surface of the receiver member includes a non-threaded portion proximal to the thread form that receives the one or more projections.

2. The assembly of claim 1, wherein the non-threaded portion is disposed between the thread form and a second threaded portion formed along a proximal end portion of the interior surface of the receiver member.

3. The assembly of claim 1, wherein the thread form includes one or more keyways that intersect the thread form and extend axially along the interior surface of the receiver member to facilitate movement of the one or more projections into the thread form.

4. The assembly of claim 3, wherein the keyways intersect with a proximal-facing surface of a U-shaped recess formed in the receiver member.

5. The assembly of claim 1, wherein the locking cap contacts the proximal head portion of the threaded shank when in the locked configuration.

6. The assembly of claim 1, wherein the locking cap rotates a half turn to move from the unlocked configuration to the locked configuration.

7. The assembly of claim 1, wherein the locking cap further comprises a drive feature on a proximal surface thereof.

8. The assembly of claim 1, further comprising a spring clip seated within a groove formed in the interior surface of the receiver member and configured to impart a drag force to the proximal head portion of the threaded shank.

9. The assembly of claim 1, further comprising:
   a spinal fixation rod disposed within a U-shaped recess formed in the receiver member proximal to the locking cap; and
   a set screw threadably coupled to the receiver member proximal to the spinal fixation rod.

10. The assembly of claim 9, wherein the spinal fixation rod contacts the locking cap and the set screw contacts the spinal fixation rod.

11. The assembly of claim 1, wherein the one or more projections includes two opposed projections.

12. The assembly of claim 1, wherein a distal-facing surface of the locking cap has a profile complementary to a shape of the proximal head portion of the threaded shank.

13. The assembly of claim 12, wherein the proximal head portion of the threaded shank has a spherical shape.

14. The assembly of claim 1, where the width of the one or more projections extends through a radial arc of less than about 45'.

15. A surgical method, comprising:
   disposing a threaded shank within a receiver member such that the threaded shank and receiver member can move polyaxially relative to one another;
   distally advancing a unitary locking cap into the receiver member through a proximal-facing opening past a non-threaded portion of an interior surface of the receiver member such that one or more projections having a width that extends through a radial arc of less than about 90° that are formed on an exterior surface of the locking cap pass through one or more keyways formed in the interior surface of the locking cap and pass into a thread form in the interior surface of the receiver member; and
   rotating the locking cap to move between an unlocked configuration, in which the receiver member can move polyaxially relative to the threaded shank, and a locked configuration, in which the receiver member is prevented from moving relative to the threaded shank.

16. The method of claim 15, further comprising implanting the threaded shank in a patient.

17. The method of claim 16, wherein the threaded shank is implanted in a vertebra.

18. The method of claim 17, further comprising performing any of a derotation maneuver or a distraction maneuver after rotating the locking cap to move to the locked configuration.

19. The method of claim 18, further comprising placing a spinal fixation rod within a U-shaped recess of the receiver member after rotating the locking cap to move to the locked configuration.

20. The method of claim 19, further comprising threading a set screw into a threaded proximal end portion of the interior surface of the receiver member such that the set screw contacts the spinal fixation rod and the spinal fixation rod contacts the locking cap.

21. The method of claim 15, wherein the locking cap is rotated about a quarter turn to move between the unlocked configuration and the locked configuration.

22. A bone screw assembly, comprising:
- a threaded shank having a proximal head portion;
- a receiver member disposed around the proximal head portion such that a distal portion of the threaded shank extends through a hole formed in a distal end of the receiver member; and
- a locking cap disposed in the receiver member proximal to the proximal head portion of the threaded shank, the locking cap including one or more projections formed on an outer surface thereof that are disposed within a thread form on an interior surface of the receiver member;
- wherein the locking cap moves between an unlocked configuration, in which the receiver member can move polyaxially relative to the threaded shank, and a locked configuration, in which the receiver member is prevented from moving relative to the threaded shank;
- wherein the interior surface of the receiver member includes a non-threaded portion proximal to the thread form that receives the one or more locking cap projections;
- wherein the thread form includes one or more keyways that intersect the thread form and extend axially along the interior surface of the receiver member to facilitate movement of the one or more projections into the thread form; and
- wherein the keyways intersect with a proximal-facing surface of a U-shaped recess formed in the receiver member.

23. A surgical method, comprising:
- disposing a threaded shank having a proximal head portion within a receiver member such that the threaded shank and receiver member can move polyaxially relative to one another;
- distally advancing a locking cap into the receiver member through a proximal-facing opening past a non-threaded portion of an interior surface of the receiver member such that one or more projections formed on an exterior surface of the locking cap pass through one or more keyways formed in the interior surface of the locking cap and pass into a thread form in the interior surface of the receiver member, the one or more projections being disposed proximal to the proximal head portion; and
- rotating the locking cap to move between an unlocked configuration, in which the receiver member can move polyaxially relative to the threaded shank, and a locked configuration, in which the receiver member is prevented from moving relative to the threaded shank.

* * * * *